United States Patent [19]

Lafon

[11] Patent Number: 4,680,302
[45] Date of Patent: Jul. 14, 1987

[54] 1-ALKYL-3-HYDROXY-3-PHENYLPIPERIDINES

[75] Inventor: Louis Lafon, Paris, France

[73] Assignee: Laboratoire L. Lafon, France

[21] Appl. No.: 823,595

[22] Filed: Jan. 29, 1986

[30] Foreign Application Priority Data

Feb. 1, 1985 [FR] France ............................. 85 01410
Jul. 10, 1985 [FR] France ............................. 85 10550

[51] Int. Cl.$^4$ ................. C07D 211/42; A61K 31/445
[52] U.S. Cl. ................................. 514/327; 546/216
[58] Field of Search ..................... 546/216; 514/327

[56] References Cited

U.S. PATENT DOCUMENTS

| 2,589,943 | 3/1952 | Jensen | 546/216 |
| 4,263,438 | 4/1981 | Althuis et al. | 546/216 |
| 4,382,942 | 5/1983 | Nedelec et al. | 546/342 |

FOREIGN PATENT DOCUMENTS

| 672114 | 10/1963 | Canada | 546/217 |
| 1455825 | 9/1966 | France . | |
| 2496099 | 6/1982 | France . | |
| 576962 | 4/1946 | United Kingdom | 546/217 |
| 1049564 | 11/1966 | United Kingdom | 546/217 |

OTHER PUBLICATIONS

M. A. Iorio et al, Tetrahedron, vol. 26 (1970), pp. 5519–5527.
Aldo Balsamo et al, Eur. J. Med. Chem.–Chimica Therapeutica, Mar.–Apr., 1981, vol. 16(2), pp. 163–169.
Uli Hacksell et al, J. Med. Chem. (1981) vol. 24, pp. 1475–1482.
B. A. Hemsworth et al, J. Pharm. Pharmacol. (1975), vol. 27, Suppl. 64P.
H. W. Bersch et al, Tetrahedron Letters, No. 11 (1966), pp. 1141–1144.
R. V. Stevens et al, Jour. Chem. Soc., Chem. Commun., (1975) No. 16, p. 682.

*Primary Examiner*—Norma S. Milestone
*Attorney, Agent, or Firm*—Jones, Day, Reavis & Pogue

[57] ABSTRACT

The present invention relates to 1-alkyl-3-hydroxy-3-phenylpiperidine derivatives of the formula

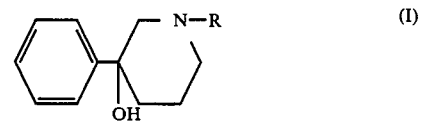

wherein R is a $C_2$–$C_4$ alkyl group, and their addition salts.

These derivatives are useful as pharmaceuticals, especially as CNS-antidepressants.

They can be prepared in accordance with the following reaction (wherein X is a halogen atom and R is defined as indicated above):

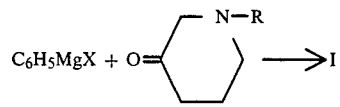

3 Claims, No Drawings

1-ALKYL-3-HYDROXY-3-PHENYLPIPERIDINES

FIELD OF THE INVENTION

The present invention relates, by way of new industrial products, to 3-hydroxy-3-phenylpiperidine derivatives, namely 1-alkyl-3-hydroxy-3-phenylpiperidines of the formula I hereinafter and their addition salts. It relates also to the method of preparation of these new products which are useful as (i) intermediate compounds and (ii) substances which are active in therapy especially in view of their anti-depressive properties on the central nervous system (CNS).

PRIOR ART

It is known that 3-hydroxy-3-phenylpiperidine derivatives, in which the phenyl ring is always substituted by halogen atoms, alkyl groups and/or alkoxy groups, have been proposed in the past as synthesis intermediate products.

In particular FR-A-2 496 099 discloses 3-hydroxy-3-(3-methoxyphenyl)-piperidine and 3-hydroxy-3-(3,4-dimethoxyphenyl)-piperidine as intermediate compounds in the preparation of N-alkyl-3-(substituted phenyl)-1,2,5,6-tetrahydropyridines; and U.S. Pat. No. 4,263,438 cites some other derivatives of the 3-hydroxy-3-phenylpiperidine type in which the phenyl ring is disubstituted (an OH, alkoxy or phenoxy group in ortho position, and an alkyleneoxyalkyl group in para position).

FR-A-1 455 825 also mentions as intermediate compounds N-alkyl-4-(halogenophenyl)-4-hydroxypiperidines.

OBJECT OF THE INVENTION

According to the invention are provided new 1-alkyl-3-hydroxy-3-phenylpiperidine derivatives, which are structurally different from the products of the above cited prior art, exhibit interesting properties as pharmaceuticals, especially as antidepressants for the CNS, and are also useful as synthesis intermediate compounds.

DETAILED DISCLOSURE OF THE INVENTION

The new derivatives according to the invention are characterized in that they are selected from the group comprising (a) the 1-alkyl-3-hydroxy-3-phenylpiperidines of the formula

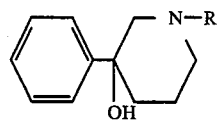
(I)

wherein R is a $C_2$–$C_4$ alkyl group; and,
(b) addition salts thereof.

The expression "addition salts" is understood here as meaning firstly the acid addition salts obtained by reacting the free base of the formula I with inorganic or organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the base of the formula I. $CH_3I$ and $CH_3Cl$ may be mentioned in particular among the compounds making it possible to obtain ammonium salts. In general terms, the acid addition salts are preferred to the ammonium salts.

A number of compounds according to the invention have been collated in Table I below without in any way implying a limitation.

TABLE I

| Product | Code Number | R | F(c) |
|---|---|---|---|
| Ex. 1(a) | — | $CH(CH_3)_2$ | 194° C.(d) |
| Ex. 2(a) | CRL 41 098 | $CH_2CH_3$ | 161° C. |
| Ex. 3(b) | — | $CH_2CH_3$ | — |
| Ex. 4(a) | — | $C(CH_3)_3$ | — |

Notes
(a)hydrochloride
(b)methanesulfonate
(c)melting point (inst.)
(d)with decomposition Amongst the $C_2$–$C_4$ alkyl groups of R, which are suitable according to the invention can be cited in particular the $CH_2CH_3$, $CH(CH_3)_2$ and $C(CH_3)_3$ groups.

The preferred compounds according to the invention in view of their therapeutical properties are the 1-ethyl-3-hydroxy-3-phenylpiperidine and its non-toxic addition salts.

The compounds according to the invention can be prepared in accordance with a method known per se, by the application of classical reaction mechanisms. The method recommended here consists in reacting a phenylmagnesium halide of the formula

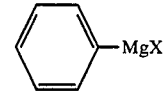
(II)

wherein X is a halogen atom (in particular Cl, Br or I, or preferably Br) with a 3-piperidinone compound of the formula

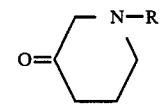
(III)

wherein R is defined as indicated above, for at least 0,25 h, at a temperature comprised between 0° C. and 25° C., under a nitrogen atmosphere, in an inert solvent in particular selected from ethers (such as dimethyl ether, diethyl ether, diisopropyl ether) tetrahydrofuran, and mixtures thereof.

In practice the 3-piperidinone previously dissolved in an inert solvent is introduced into a solution of phenylmagnesium halide in an inert solvent which is the same or different from the solvent of the 3-piperidinone, at a temperature of 0° C. which is maintained the period of the introduction of said 3-piperidinone, then the reaction medium is left to come back to room temperature (15°–20° C.). In general an excess of $C_6H_5MgX$ with respect to stoichiometric conditions will be used, in particular 2 to 3 mols of II for 1 mol of III.

Alternatively, the compounds of the formula I can be prepared according to the reaction

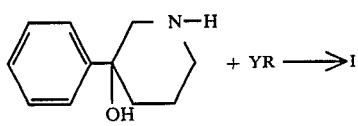

wherein Y is a halogen atom (in particular F, Cl, Br or I, and preferably I) and R is defined as indicated above.

The compounds of the formula I are useful as CNS-antidepressants and present the advantage of being less toxic than the corresponding N-alkyl-3-phenyl-1,2,5,6- and 1,4,5,6-tetrahydropyridine derivatives of the formulae

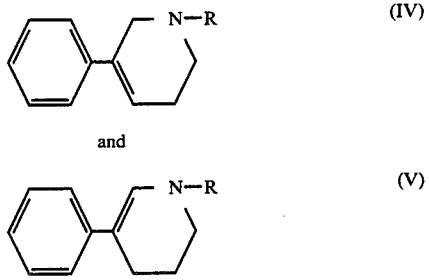

disclosed in French patent application No. 85 01410 of Feb. 1, 1985, which are CNS-active (mainly as sedative agents) and which can be prepared from the said compounds of formula I by means of a dehydratation reaction.

According to the invention is provided a therapeutical composition which contains, in association with a physiologically acceptable excipient, at least one compound of the formula I or one of its non-toxic addition salts as the active principle.

Of course, in a composition of this type, the active principle is present in a pharmaceutically effective amount.

On the other hand is recommended the utilisation of compounds of the formula I and their non-toxic addition salts for obtaining a CNS antidepressive medicament destined to be used in human therapy against depressions and depressive states.

Further advantages and characteristics of the invention will be understood more clearly on reading the following description of preparative examples and results of pharmacological tests; these data as a whole do not imply a limitation but are given by way of illustration.

PREPARATION I

Obtention of 1-ethyl-3-hydroxy-3-phenylpiperidine hydrochloride

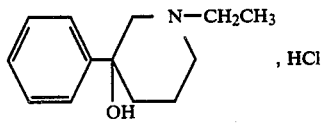

(Example 2, Code Number: CRL 41 098).
Alternative nomenclature: N-ethyl-3-phenyl-3-piperidinol hydrochloride.

62 ml of a phenylmagnesium bromide 3M solution in diethyl ether were poured, under a nitrogen atmosphere, into a solution cooled by means of an ice+salt bath of 0.153 mol of 1-ethyl-3-piperidinone in diethyl ether. After the $C_6H_5MgBr$ 3M addition was achieved, the reaction medium was left in order that its temperature raised to the room temperature, then poured into a water-ice mixture. After decantation the ether phase was collected, washed with water, dried over $MgSO_4$ then filtered. From the filtrate thus obtained, the expected hydrochloride was precipitated by means of HCl-containing ethanol. By recristallization from an acetone-ethanol (1:1) v/v mixture 1.07 g (yield: 2.7%) of CRL 41 098 were obtained. Melting point (inst.)=161° C.

Analysis $\begin{cases} \% \text{ Cl}^- \text{ measured: } 14.88\% \\ \% \text{ Cl}^- \text{ theoretical: } 14.70\% \end{cases}$

PREPARATION II

Obtention of 1-isopropyl-3-hydroxy-3-phenylpiperidine hydrochloride (Example 1)
Alternative nomenclature: N-isopropyl-3-phenyl-3-piperidinol hydrochloride.

By following the procedure indicated in Preparation I and replacing the 1-ethyl-3-piperidinone with the 1-isopropyl-3-piperidinone, the 1-isopropyl-3-hydroxy-3-phenylpiperidine was obtained.

Melting point (inst.)=194° C. (with decomposition).

PREPARATION III

Obtention of 1-isopropyl-3-hydroxy-3-phenylpiperidine hydrochloride (Example 1)
A reaction medium comprising 28.3 g (0.132 mol) of 3-hydroxy-3-phenylpiperidine, 24.77 g (0.146 mol) of isopropyl iodide, 46.4 g (0.438 mol) of $CO_3Na_2$ and 300 ml of $H_2O$ was brought to reflux temperature for 4 hours. After cooling, extraction with ether, washing with water the ether phase drying said ether phase over $MgSO_4$ and filtering of $MgSO_4$, the expected hydrochloride was precipitated from the filtrate thus obtained, by addition of HCl-containing ethanol. By recrystallization from acetone-ethanol (1:1) v/v, 23 g (yield: 68%) of 1-isopropyl-3-hydroxy-3-phenylpiperidine hydrochloride were obtained. Melting point (inst.)=194° C. (with decomposition).

The results of the tests which were undertaken with the product of Example 2 (CRL 41 098) which is the preferred compounds according to the invention have been summarized below. In these tests, unless stated otherwise, the product was administered intraperitoneally in solution in distilled water at pH 5, in a volume of 20 ml/kg to male mice.

I. TOXICITY

It is observed that CRL 41 098 administered by i.p. route to male mice at doses of 16 mg/kg to 128 mg/kg does not cause the death of the animals. The LD-0 (maximum non-lethal dose) is therefore higher than 128 mg/kg. The LD-50 value is of the order of about 250 mg/kg.

By comparison the tetrahydropyridine derivatives obtained from the compounds of the formula I by dehydratation are more toxic. In particular per i.p. route on male mice (i) the LD-0 and LD-50 of CRL 41 244 [N-isopropyl-3-phenyl-1,2,5,6-(or 1,4,5,6-)tetrahydropyridine hydrochloride] are respectively of the order of 30 mg/kg and 90 mg/kg, and (ii) the LD-30 of CRL 41 124 [N-ethyl-3-phenyl-1,2,5,6-(or 1,4,5,6-)tetrahydropyridine hydrochloride] is of the order of about 60 mg/kg.

II. OVERALL BEHAVIOR AND REACTIVITIES

Groups of 6 animals are observed before and then 15 Minutes, 30 minutes, 1 hour, 2 hours, 3 hours and 24 hours after the administration of CRL 41 098. In mice, the observations made at the following doses are:

1 and 4 mg/kg:
  no distinct modification of behavior, reactivities, rectal temperature variations, and pupillary diameter variations with respect to control animals receiving only water;

16 mg/kg:
  sedation 0.5 h after administration, and
  hypothermia (maximum: −2.5° C., 0.5 h after administration) for a period of 3 hours; and, 64 mg/kg:
  sedation for about 0.5 h,
  hypothermia (maximum: −2.7° C., 0.5 h after administration) for a period of 3 hours.

III. ACTION ON RECTAL TEMPERATURE

The rectal temperature of mice (6 animals per dose) is measured every 30 minutes during 3 h, after administration of CRL 41 098 per i.p. route. It is found that at the doses of 16 mg/kg and (mainly) 64 mg/kg, CRL 41 098 induces a hypothermia having a duration of from 1 h (16 mg/kg) to 1.5 h (64 mg/kg).

IV. INTERACTION WITH APOMORPHINE

Groups of 6 mice receive CRL 41 098 half an hour before the subcutaneous injection of 1 or 16 mg/kg of apomorphine. It is found that, at the dose of 64 mg/kg, CRL 41 098 antagonizes the hypothermia induced by apomorphine, without modifying the righting behavior and stereotypies caused by apomorphine.

V. INTERACTION WITH RESERPINE

Four hours after the intraperitoneal injection of 2.5 mg/kg of reserpine, groups of 6 mice receive CRL 41 098 by intraperitoneal administration. It is observed that, at doses of 64 mg/kg and 256 mg/kg, CRL 41 098 opposes the hypothermia induced by reserpine. However the antagonism distinctly appears at doses of 16 and 64 mg/kg. The ptosis induced by reserpine is not modified significantly.

VII. INTERACTION WITH OXOTREMORINE

CRL 41 098 is administered to groups of 6 mice half an hour before the intraperitoneal injection of 0.5 mg/kg of oxotremorine.

(1) Action on the temperature

At doses of 4, 16 and 64 mg/kg, CRL 41 098 antagonizes the hypothermic effect of oxotremorine.

(2) Action on the trembling

The trembling due to oxotremorine is not appreciably modified by CRL 41 098.

(3) Action on the peripheral cholinergic symptoms

CRL 41 098 does not modify the peripheral cholinergic stimulation signs induced by oxotremorine.

VII. ACTION ON THE SPONTANEOUS MOTILITY

Half an hour after they have received CRL 41 098 the mice (6 per dose, 12 control animals) are placed in an actimeter, where their motility is recorded for 30 minutes. It is found that, at the dose of 16 and mainly at the dose of 64 mg/kg, CRL 41 098 causes an appreciable decrease in the spontaneous motor activity of mice.

All the results clearly point out the interest of CRL 41 098 as antidepressant agent. In the neuropsychopharmacological profile of said CRL 41 098 are also observed sedative effects.

Further experiments to complete the neuropsychopharmacological results were performed.

TERATOGENIC STUDY

Assays undertaken on rabbits (group of 10 female animals per dose; 15 control animals) according to a protocol comprising
  administration of CRL 41 098 by gastrogavage at daily doses of 0, 10, 50 and 100 mg/kg from day 5 to day 18 of gestation, followed by
  a cesarean carried out on day 28 of gestation, pointed out that, unlike certain 3-phenylmorpholine derivatives known in the prior art, CRL 41 098 is devoid of a teratogenic effect.

What is claimed is:

1. 1-Ethyl-3-hydroxy-3-phenylpiperidine and its addition salts.

2. A therapeutical composition which comprises, in association with a physiologically acceptable excipient, a pharmaceutically effective amount of 1-ethyl-3-hydroxy-3-phenylpiperidine according to claim 1 or one of its non-toxic addition salts.

3. A method of treatment of depression which comprises administering to a person in need of such a treatment an antidepressive effective amount of 1-ethyl-3-hydroxy-3-phenylpiperidine according to claim 1 or one of its non-toxic addition salts.

* * * * *